United States Patent [19]

Yoneoka et al.

[11] Patent Number: 5,399,745

[45] Date of Patent: Mar. 21, 1995

[54] PROCESS FOR PRODUCING METHYL FORMATE

[75] Inventors: Mikio Yoneoka; Takeo Ikarashi; Kumiko Watabe; Kenji Nakamura, all Niigata, Japan

[73] Assignee: Mitsubishi Gas Chemical Company, Inc., Tokyo, Japan

[21] Appl. No.: 224,045

[22] Filed: Apr. 7, 1994

[30] Foreign Application Priority Data

May 17, 1993 [JP] Japan .................. 5-114758

[51] Int. Cl.$^6$ ............................. C07C 68/04
[52] U.S. Cl. ................................. 560/239
[58] Field of Search ........................ 560/239

[56] References Cited

U.S. PATENT DOCUMENTS

| | | |
|---|---|---|
| 4,126,748 | 11/1978 | Scholz et al. |
| 4,149,009 | 4/1979 | Yoneoka et al. ............ 560/239 |
| 4,232,171 | 11/1980 | Yoneoka et al. ............ 560/239 |
| 4,319,037 | 3/1982 | Yoneoka ...................... 560/239 |
| 4,480,122 | 10/1984 | Horlenko et al. ........... 560/239 |
| 5,144,062 | 9/1992 | Chen et al. ................... 560/239 |
| 5,194,675 | 3/1993 | Joerg et al. |

FOREIGN PATENT DOCUMENTS 0026415  4/1981  European Pat. Off. .

*Primary Examiner*—Arthur C. Prescott
*Attorney, Agent, or Firm*—Frishauf, Holtz, Goodman & Woodward

[57] ABSTRACT

There are disclosed a process for producing methyl formate by dehydrogenating methanol in liquid phase in the presence of a solid catalyst and a process according thereto wherein a gas ($N_2$, $H_2$, CO, etc.) is continuously blown into the liquid phase from outside, and the gas along with the reaction product are continuously withdrawn outside the reaction system from the gaseous phase directly or through a cooler. By virtue of the liquid-phase reaction in the above process, as compared with the conventional gaseous phase reaction, the reaction temperature can be lowered, the reaction gas rich in the objective methyl formate rather than methanol is obtained by continuously withdrawing the resultant methyl formate outside the reaction system and accordingly, a single pass yield higher than that at the thermodynamical equilibrium-value is assured, whereby energy saving is made possible.

11 Claims, No Drawings

PROCESS FOR PRODUCING METHYL FORMATE

BACKGROUND OF THE INVENTION

1. Field of the Invention

The present invention relates to a process for producing methyl formate by the dehydrogenation of methanol.

Methyl formate is a product for chemical industries which is important as an intermediate to be used for producing organic chemicals such as dimethylformamide and formic acid, carbon monoxide and the like.

2. Description of Related Arts

It is known that methyl formate is produced by a process wherein methanol is carbonylized into methyl formate under pressure by the use of a catalyst such as sodium alcoholate according to the chemical equation $CH_3OH + CO \; HCOOCH_3$ (1) or a process in which methanol is catalytically dehydrogenated into methyl formate according to the chemical equation $2CH_3OH \; HCOOCH_3 + 2H_2$ (2).

The production of methyl formate by the dehydrogenation of methanol is industrially put into practice at the present time due to the recent progress of development of catalysts and a variety of catalysts proposed. There are disclosed, as examples of dehydrogenation catalyst, a catalyst comprising copper and an element belonging to group 3a of the periodic table in Japanese Patent Publication No. 6412/1981; a catalyst comprising copper, an actinide and an rare-earth element in Japanese Patent Publication No. 46819/1978; a catalyst comprising copper, zinc, an oxide of aluminum and zirconium in Japanese Patent Publication No. 46821/1978; a catalyst comprising copper and a cement in Japanese Patent Publication No. 15820/1982; a catalyst comprising copper, calcium and a zirconium compound in Japanese Patent Publication No. 44655/1982; and a catalyst comprising copper, zinc, an oxide of aluminum, an alkali-metal compound and a phosphorus compound in Japanese Patent Publication No. 33418/1984 and Japanese Patent Application Laid-Open No. 151047/1991.

The production of methyl formate by the dehydrogenation of methanol usually attains only several tens percent of yield because of equilibrium conditions. In the case of carrying out the dehydrogenation reaction under pressure taking into consideration the collection of low boiling methyl formate, the yield thereof is further lowered. In the case of effecting the reaction in gaseous phase, therefore, it is forced to cool reactor outlet gas for separating gas from liquid, separate methyl formate from the mixture of the condensed methyl formate and unreacted methanol, and thereafter recycle a large amount of the separated methanol through the dehydrogenation reaction step, causing a disadvantage that a large amount of energy is required. If the problems of such low conversion efficiency in one pass system and the forced recycle of a large amount of methanol are solved, it is made possible to more efficiently produce methyl formate by the dehydrogenation of methanol.

In the production of methyl formate by the dehydrogenation of methanol in gaseous phase, the above-mentioned equilibrium restriction makes it impossible to achieve a high yield of methyl formate in one pass system.

Accordingly, in order to advantageously proceed with the reaction, the equilibrium restriction must be overcome. For the aforesaid purpose, for example, methyl formate or hydrogen as a reaction product may be withdrawn outside the reaction system to enable the reaction to proceed towards the formation of methyl formate. The aforementioned idea is disclosed, for example, in Japanese Patent Application Laid-Open No. 235846/1990. According to the disclosure therein, by the use of a reactor equipped with a hydrogen separating membrane, the hydrogen produced by the dehydrogenation of methanol is continuously withdrawn through the separating membrane outside the reaction system so as to proceed with the reaction. However, according to the working examples therein, the above-mentioned method shows improvements in methanol conversion efficiency and yield of methyl formate of only 2 to 13%, when compared at the same reaction temperature.

Under such circumstances, intensive research and investigation were accumulated by the present inventors, and finally the present invention has been accomplished.

SUMMARY OF THE INVENTION

The present invention provides a process for producing methyl formate by the dehydrogenation of methanol characterized in that methanol is dehydrogenated in liquid-phase reaction system.

Specifically, there have been developed by the present invention, (1) a process for producing methyl formate by the dehydrogenation of methanol in the presence of a solid catalyst which process comprises dehydrogenating methanol in liquid-phase reaction system; (2) a process for producing methyl formate by the dehydrogenation of methanol in the presence of a solid catalyst which process comprises dehydrogenating methanol in liquid-phase reaction system by continuously withdrawing the reaction product in gaseous phase outside the reaction system; (3) a process according to the above-mentioned item (2) which comprises dehydrogenating methanol in liquid-phase reaction system by continuously introducing into the reaction system, a gas selected from among nitrogen, hydrogen, carbon monoxide, helium, argon and a mixture of at least two of them, especially oxygen-free gas and at the same time, continuously withdrawing the reaction product in gaseous phase outside the reaction system; (4) a process according to the above-mentioned item (2) or (3) which comprises dehydrogenating methanol in liquid-phase reaction system by a method in which the gas introduced into the reaction system and the reaction product are cooled to condense a part of methanol and reflux the condensed methanol to the reaction liquid phase, and thereby the gas which is rich in methyl formate rather than methanol is taken out of the reaction system.

DESCRIPTION OF PREFERRED EMBODIMENT

A process for producing methyl formate from methanol in liquid phase has already been proposed. For example, oxidative dehydrogenation process instead of dehydrogenation process is exemplified by a method of oxidizing methanol by using Pd as the catalyst in J. Chem. Soc. Jpn., Ind. Chem. Sect. vol 71, No. 10, page 1638 (1968), and a method of continuously reacting molecular oxygen with methanol in liquid phase at a high temperature in the presence of a catalyst composed of a soluble chromium compound in Japanese Patent Application Laid-Open No. 203034/1982.

The method of dehydrogenating methanol in liquid phase is exemplified by a method of dehydrogenating methanol in a solution of $RuCl_3$ in $CH_3OH$ in the presence of $CH_3ONa$ in J. Mol Catal 67 2, PP. 185 to 190 (1991), which process however, is not intended for the production of methyl formate and is not clear in the future prospect of its practicability.

In such circumstance, the present invention provides an entirely novel method for dehydrogenating methanol. That is to say, the reaction in liquid phase by the use of a solid catalyst according to the present invention dispenses with the heat of vaporization for methanol and need not any heat but the sensible heat required for heating the liquid to the reaction temperature, thus enabling energy saving.

The process for producing methyl formate relates to a method for dehydrogenating methanol by reacting methanol in liquid phase and withdrawing outside the reaction system, the hydrogen and methyl formate that are formed by the reaction and transferred to the gaseous phase.

The reaction products can be withdrawn outside the reaction system by the use of hydrogen alone which is formed by the reaction or by the method in which a gas or mixed gas is continuously introduced into the reaction system and then continuously withdrawn outside the reaction system while the reaction pressure is kept constant, and the methyl formate and hydrogen that are formed by the reaction are taken out of the gaseous phase in the system. The latter method is particularly favorable and enables the reaction to advantageously proceed towards the formation of objective methyl formate as the reaction products are withdrawn outside the reaction system from the methanol dehydrogenation reaction zone in liquid phase.

The process according to the present invention enables the dehydrogenation reaction in liquid phase to proceed advantageously and assures the performance results superior to those of the equilibrium value by not only withdrawing the hydrogen formed by the reaction as well as the methyl formate vapor transferred to the gaseous phase out of a reactor but also introducing a gas or mixed gas into the reaction system and withdrawing the same forcibly and continuously outside the reaction system. In this case, the reaction gas can be taken out of the reactor in the form of gas as it is without being condensed by thermally insulating the connection between the reactor and a pressure regulator which regulates the reaction pressure. It is also possible to obtain a reaction gas rich in methyl formate rather than methanol by cooling the reaction gas in the connection between the reactor and the pressure regulator which regulates the reaction pressure so that a part of methanol gas in the outlet gas is condensed and the condensed methanol is refluxed to the liquid-phase reaction zone.

There is employed, in the process according to the present invention, a solid catalyst, which is not specifically limited but may be selected for use from conventional catalysts which have heretofore been proposed. Examples of such catalyst include various copper-containing catalysts such as Raney copper catalyst and copper/chromium based catalyst. The reaction temperature according to the present invention is 100° to 300° C., preferably 150° to 250° C. The reaction pressure according to the present invention is not specifically limited provided that liquid phase is maintained in the reaction system at a given reaction temperature.

It is necessary that the gas to be introduced into a reactor does not exert such evil influence as will liquefy under the reaction conditions or react with the starting raw material and/or any of the reaction products. Examples of the usable gases include a gas selected from among nitrogen, hydrogen, carbon monoxide, helium, argon and a mixture of at least two of them, especially oxygen-free gas. The gas to be introduced into the reaction system, when blown into the liquid phase, is effective in assisting the contact between methanol and the catalyst and also in transferring the methyl formate which is formed in the liquid phase to the gaseous phase, thus making the gas introduction system favorable. Alternatively the gas can be introduced into the gaseous phase. The amount of the gas to be introduced into the reaction system is not specifically limited but can be an arbitrary amount. However, the introduction of an excessively large amount of gas is not advantageous, since it lowers the efficiencies of collection and recovery systems of the objective methyl formate.

The reaction method according to the present invention can be put into practice by any of batch-wise system, semibatch-wise system and flow system. The reaction system is preferably stirred in order to efficiently bring the catalyst in the form of powder or small particle into contact with liquid methanol. The stirring method is not specifically limited but can preferably be exemplified by a method wherein agitational blades are rotated and a method wherein agitational blades are reciprocated in vertical direction.

The method according to the present invention is advantageous, in comparison with the conventional gaseous phase method, in that the heat of vaporization for methanol is obviated, the reaction temperature can be lowered and thereby the required energy can be saved by virtue of carrying out the reaction in liquid phase during the production of methyl formate by the dehydrogenation of methanol. In contrast to the conventional gaseous phase method which is restricted by equilibrium conditions, the method according to the present invention is capable of attaining a yield of methyl formate higher than that restricted by the equilibrium under the same reaction conditions by virtue of shifting the equilibrium towards the favorable side by introducing a gas or mixed gas into the reaction system. The above-mentioned advantages render the method of the present invention extremely significant from the industrial viewpoint.

In the following, the present invention will be described in more detail with reference to examples, which however, shall not be construed to limit the present invention thereto.

EXAMPLE 1

In a 100 ml stainless-steel (SUS-316) made autoclave of shaking type were placed 31.6 g of methanol and 10 g of Cu-Zn-Al catalyst which had been reduced and crushed to 60 to 80 mesh. Then, hydrogen gas was fed into the autoclave up to an autoclave pressure of 10 $kg/cm^2$ to proceed with reaction at 190° C. for 60 minutes under heating and shaking. Subsequently the autoclave was cooled, and the reaction liquid was taken out of the autoclave and analysed. As a result, methyl formate was present therein in a concentration of 0.4% by weight.

EXAMPLE 2

The procedure in Example 1 was repeated except that carbon monoxide gas in place of hydrogen gas was fed into the autoclave and the reaction was carried out at 200° C. instead of 190° C. As the result of analysis for the reaction liquid, methyl formate was present therein in a concentration of 1.4% by weight.

EXAMPLE 3

The procedure in Example 1 was repeated except that 11.6 g of Raney copper was employed as the catalyst in place of 10 g of Cu-Zn-Al catalyst and nitrogen gas in place of hydrogen as was fed into the autoclave. As the result of analysis for the reaction liquid, methyl formate was present therein in a concentration of 1.0% by weight.

EXAMPLES 4 to 8

The reaction was carried out in flow system by the use of a vertically stirring type 300 ml autoclave lined inside with titanium. Specifically, the autoclave was charged with 200 ml of methanol and a catalyst as given in Table 1 and heated under vertical stirring, while fresh methanol was fed therein at a constant feed rate as given in Table 1. Concurrently, a gas was introduced into the liquid phase in the autoclave and taken out thereof through a cooler so that the reaction pressure is kept constant. The results of analysis and performance are given in Table 1.

EXAMPLE 9

The reaction was carried out in the same manner as in Example 7 except that nitrogen gas was not introduced into the reaction system. Investigation was made on the concentrations of methanol and methyl formate each in the gaseous phase. As the result, methanol and methyl formate were present in concentrations of 83.1% and 10.6% by volume, respectively under the conditions including a liquid phase temperature of 205° C., a gaseous phase temperature of 196° C. and a reaction pressure of 48.5 kg/cm$^2$. Although the gaseous phase in the autoclave was rich in methanol as indicated above, the reaction product rich in methyl formate rather than methanol could be obtained by introducing a gas into the reaction system and cooling the introduced gas at the time of taking out of the autoclave in the same manner as in Examples 4 to 8.

What is claimed is:

1. A process for producing methyl formate by the dehydrogenation of methanol which process comprises effecting said dehydrogenation in liquid-phase reaction system in the presence of a solid catalyst.

2. The process according to claim 1 wherein the reaction product in the form of gaseous phase is continuously withdrawn outside the reaction system from the system.

3. The process according to claim 1 wherein a gas selected from the group consisting of nitrogen, hydrogen, carbon monoxide, helium, argon and a mixture of at least two of them is continuously introduced in the reaction system and the reaction product in the form of gaseous phase is continuously withdrawn outside the reaction system from the system.

4. The process according to claim 1 wherein an oxygen-free gas selected from the group consisting of nitrogen, hydrogen, carbon monoxide, helium, argon and a mixture of at least two of them is continuously introduced in the reaction system and the reaction product in the form of gaseous phase is continuously withdrawn outside the reaction system from the system.

5. The process according to claim 1 wherein a gas selected from the group consisting of nitrogen, hydrogen and carbon monoxide is continuously introduced in the reaction system and the reaction product in the form of gaseous phase is continuously withdrawn outside the reaction system from the system.

6. The process according to claim 3 wherein the gas is introduced into liquid phase of the reaction system.

7. The process according to claim 3 wherein the gas introduced into the reaction system and the reaction product are cooled to condense a part of methanol, the condensed methanol is refluxed to the reaction liquid phase, and the gas which is rich in methyl formate rather than methanol is withdrawn outside the reaction system from the system.

8. The process according to claim 4 wherein the gas introduced into the reaction system and the reaction product are cooled to condense a part of methanol, the condensed methanol is refluxed to the reaction liquid phase, and the gas which is rich in methyl formate rather than methanol is withdrawn outside the reaction system from the system.

9. The process according to claim 1 wherein the solid catalyst is a copper-containing catalyst.

10. The process according to claim 1 wherein dehydrogenation reaction is effected at a reaction temperature in the range of 100° to 300° C.

11. The process according to claim 10 wherein the reaction temperature is in the range of 150° to 250° C.

TABLE 1

|  | Example No. | | | | |
| --- | --- | --- | --- | --- | --- |
|  | 4 | 5 | 6 | 7 | 8 |
| Catalyst | Raney copper 22 g | Cu—Zn—Al 29 g | Raney copper 40 g | Raney copper 40 g | Copper-chromium 30 g |
| Methanol Feed rate (g/hr) | 4.0 | 10.3 | 5.3 | 9.0 | 10.3 |
| Introduced gas | nitrogen | nitrogen | hydrogen | nitrogen | carbon monoxide |
| Reaction pressure (kg/cm$^2$) | 45.5 | 48.0 | 50.0 | 48.5 | 48.0 |
| Reaction temperature (°C.) | 198 | 197 | 199 | 196 | 195 |
| Amount of withdrawn gas (l/hr) | 17.1 | 64.4 | 75.3 | 79.9 | 67.3 |
| Methanol (vol %) | 1.14 | 1.42 | 0.91 | 1.32 | 1.41 |
| Methyl formate (vol %) | 5.26 | 3.63 | 1.72 | 3.04 | 4.33 |
| Methanol Conversion (mol %) | 91.6 | 87.2 | 81.1 | 83.3 | 82.6 |
| Methyl formate Yeild (mol %) | 77.1 | 65.2 | 73.1 | 77.0 | 77.5 |
| Selectivity (mol %) | 84.2 | 74.8 | 90.0 | 92.5 | 93.5 |

* * * * *